United States Patent
Willaman

(10) Patent No.: US 10,359,413 B2
(45) Date of Patent: Jul. 23, 2019

(54) SYSTEMS AND METHODS FOR MONITORING CALIBRATION OF MOISTURE SENSORS

(71) Applicant: Command Alkon Incorporated, Birmingham, AL (US)

(72) Inventor: Randall E. Willaman, Dublin, OH (US)

( * ) Notice: Subject to any disclaimer, the term of this patent is extended or adjusted under 35 U.S.C. 154(b) by 0 days.

(21) Appl. No.: 15/740,046

(22) PCT Filed: Jul. 1, 2016

(86) PCT No.: PCT/US2016/240794
§ 371 (c)(1),
(2) Date: Dec. 27, 2017

(87) PCT Pub. No.: WO2017/004569
PCT Pub. Date: Jan. 5, 2017

(65) Prior Publication Data
US 2018/0188227 A1    Jul. 5, 2018

Related U.S. Application Data

(60) Provisional application No. 62/187,726, filed on Jul. 1, 2015.

(51) Int. Cl.
*G01N 33/38* (2006.01)
*B28C 7/04* (2006.01)
(Continued)

(52) U.S. Cl.
CPC ......... *G01N 33/383* (2013.01); *B28C 7/0409* (2013.01); *G01G 23/01* (2013.01); *G01G 19/00* (2013.01)

(58) Field of Classification Search
CPC .................................................. G01N 33/383
See application file for complete search history.

(56) References Cited

U.S. PATENT DOCUMENTS 9,153,123 B2 * 10/2015 Glenn ..................... H04W 4/70
2001/0030543 A1 * 10/2001 Joshi .................... G01N 27/221
324/643
(Continued)

FOREIGN PATENT DOCUMENTS

WO    WO 9618084 A1 *  6/1996 ............. G01D 3/032
WO    2008/031152 A1    3/2008

OTHER PUBLICATIONS

Md. Nazmul Alam et al., "Concrete Moisture Content Measurement Using Interdigitated Near-Field Sensors," IEEE Sensors Journal, vol. 10, No. 7, Jul. 2010, 1243-1248, US.
(Continued)

*Primary Examiner* — Jamel E Williams
(74) *Attorney, Agent, or Firm* — Jacob W. Neu; Bradley Arant Boult Cummings LLP

(57) ABSTRACT

A method and system for calibrating moisture sensors in a concrete production plant are disclosed. The moisture sensor is in communication with a computer database through a transceiver. The moisture sensor records numerous readings of moisture for aggregate used in concrete production, which are stored in the database. Separately, a manual sample of aggregate taken from the production line is determined to have a moisture content, which is the baseline for calibrating the sensor. This record is also entered into the database. The moisture sensor reading and the manual sample record are compared for multiple iterative readings to determine whether a sensor requires further calibration.

7 Claims, 12 Drawing Sheets

(51) Int. Cl.
*G01G 23/01* (2006.01)
*G01G 19/00* (2006.01)

(56) References Cited

U.S. PATENT DOCUMENTS

| | | | | |
|---|---|---|---|---|
| 2004/0007052 A1* | 1/2004 | Belanger | ............ | G01N 33/2847 73/73 |
| 2004/0237625 A1* | 12/2004 | Rombach | ............... | G01N 25/56 73/1.06 |
| 2013/0182360 A1* | 7/2013 | Stevens | .................... | H02H 5/00 361/71 |
| 2018/0172635 A1* | 6/2018 | Lai | ....................... | G01N 27/622 |

OTHER PUBLICATIONS

Neal Cass, "Effects of Moisture Variation on Concrete Mixes and Methods to Control Final Mix Quality," 10th International Conference on Concrete Block Paving, Shanghai, Peoples Republic of China, Nov. 24-26, 2012, pp. 1-11.
EP Application No. 16818918.1, Extended European Search Report, dated Mar. 8, 2019.

* cited by examiner

SYSTEMS AND METHODS FOR MONITORING CALIBRATION OF MOISTURE SENSORS

TECHNICAL FIELD

The invention relates to the field of concrete production, and more particularly, to calibration for moisture sensors used in concrete production.

Background Art

Concrete production involves the careful mixing of water, aggregate material such as sand or gravel, and cement, together with other additives for giving the concrete particular desired characteristics. The strength of concrete depends on a number of factors including the particular type and amount of aggregate and cementitious materials used, various chemical or mineral admixtures, and the use of reinforcement such as steel bars, glass or plastic fibers. These variations in composition of the concrete are referred to as types or "families." One key factor for strength of concrete within a given family is the water-to-cement ratio ("W/C ratio"). Within a given family of concrete formulations, increasing the water present in the concrete has an inverse relationship to the final strength of the hardened concrete. In other words, where all other factors are held constant, when the W/C ratio increases, the concrete strength decreases. For this reason, the amount of water used in the concrete production process allows the designer to accurately design the strength of the finished concrete. An accurate strength prediction is particularly important in concrete design and production because concrete does not fully cure to its designed strength for a long period, conventionally defined as 28 days. If the concrete does not cure with the necessary strength, it may have to be removed and replaced, causing significant delays and cost overruns in the construction project.

Water may enter the concrete mixture through a number of pathways. Water and/or ice is introduced and mixed with the aggregate, cement, and other materials (some of which are water based) which creates a plastic material that eventually hardens into concrete. These various sources of water can be accurately measured at the time of its addition to the mix. However, the "dry" aggregate material also introduces water to the mix via particle surface and/or absorbed water, typically on the order of 2-10% of the total weight by volume. An electronic sensor is used to determine the amount of water present in the aggregate which is typically expressed as a percentage moisture content.

The moisture content of the aggregate can vary from material to material and from stockpile to stockpile ("pile") and can greatly contribute to the total water of concrete in its plastic state. First, the particular mineral composition of the aggregate material varies the water content (e.g., certain types of rock retain more moisture than others, and fine sand typically traps more moisture than coarse gravel or crushed rock). Second, aggregate is typically stored in an exposed stockpile on site at the concrete plant. After sitting for any length of time, gravity assures that aggregate at the top of the pile is much drier than aggregate at the bottom of the pile. While the pile can be occasionally mixed to more evenly redistribute the moisture throughout the pile, a consistent moisture distribution is not practically achievable. In some circumstances, the aggregate piles are sprinkled with water on a periodic or consistent basis in an attempt to maintain consistent moisture. The aggregate for a plant is usually transferred to a conveyor system feeding the plant by a front end loader. Alternatively, where there is not enough room to store a pile of aggregate on site, the aggregate is unloaded from a truck directly into the production process. The aggregate delivered by each truck may have a unique moisture profile depending on how and where it was produced and its transport time to the concrete production plant.

The effect of added water in a load of concrete due to moisture can be substantial. In a 7.6 $m^3$ (10 cubic yards) load, a one percent (1%) change in the moisture of one aggregate material results in an additional 76 liters (20 gal.) in the load. This extra water can result in the load being unsuitable for its intended purpose.

Therefore, moisture sensors within the production process at the concrete plant are necessary for obtaining an accurate reading of the moisture content of aggregate used for a particular batch of concrete. However, these sensors are typically only calibrated prior to or during installation. If a sensor becomes uncalibrated or inaccurate, this may not be known until the concrete has fully hardened and is tested to have insufficient strength, which may not be known for weeks. In the meantime, the faulty sensor can undermine the designed strength of produced concrete for all the batches produced in the interim. What is needed is a process for monitoring the calibration of a sensor over time, such that a faulty sensor can be promptly detected and either recalibrated or replaced.

DISCLOSURE OF INVENTION & INDUSTRIAL APPLICABILITY

To determine whether a moisture sensor or probe then currently in use at the mixing plant is properly calibrated, numerous iterative samples are taken and compared against a bake-out sample. The moisture sensor readings are then compared using a confidence interval as further described herein. When a subset of samples from the total set of samples taken are outside the confidence interval, and that subset exceeds a pre-determined allowed number per the number of samples taken, then the moisture sensor should be re-calibrated.

One benefit of this iterative testing process is the lower likelihood that a single outlying reading will result in a mistaken need for re-calibration, which can result in improper calibration or lost time and production due to excessive re-calibration.

Another benefit of this iterative testing process is the increased accuracy relating to the use of multiple moisture sensor readings.

Another benefit of this iterative testing process is a repeatable and verified calibration procedure.

Another benefit of this iterative testing process is the isolation of aberrant moisture sensor readings due to poorly mixed or highly stratified aggregate.

BRIEF DESCRIPTION OF DRAWINGS

It should be noted that identical features in different drawings are shown with the same reference numeral.

DETAILED DESCRIPTION AND MODES FOR CARRYING OUT INVENTION

Figure 1:
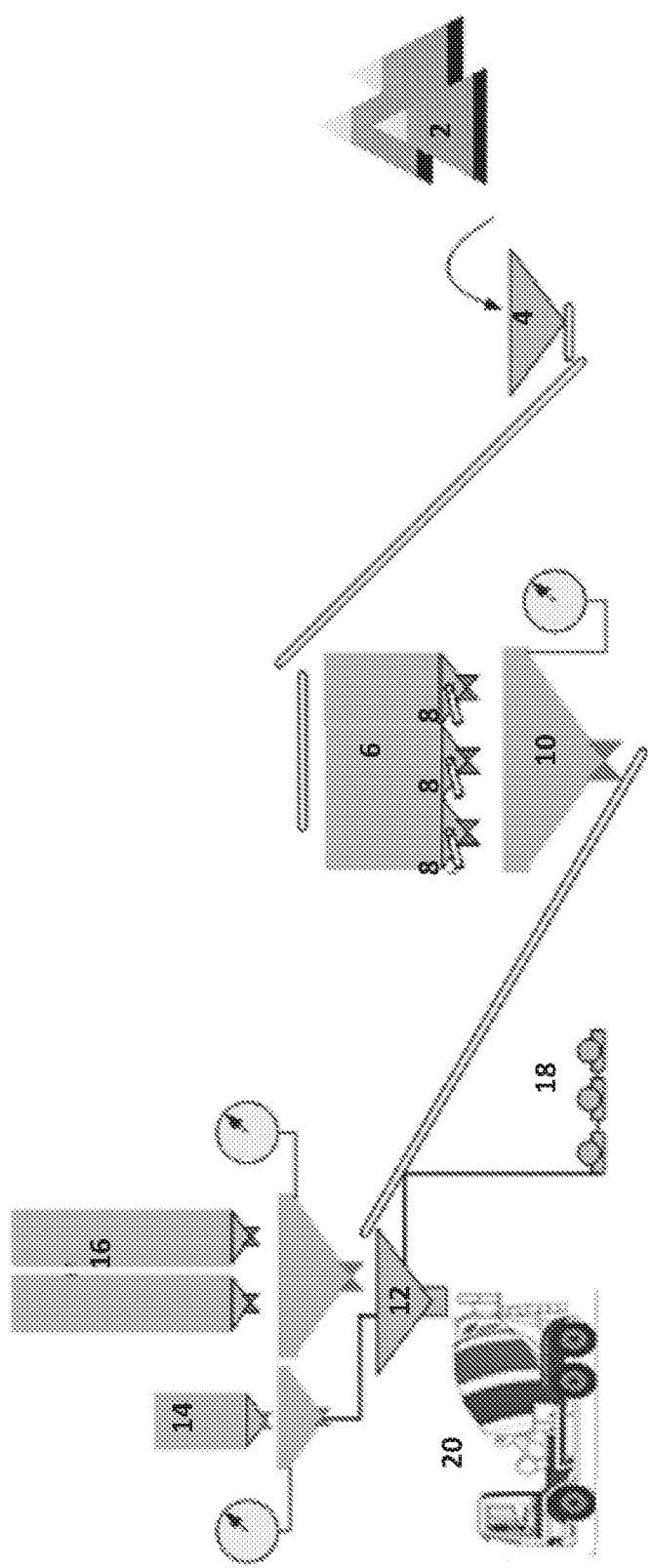
FIG. 1 depicts a general system and process for producing concrete at a concrete plant.
Figure 2A:
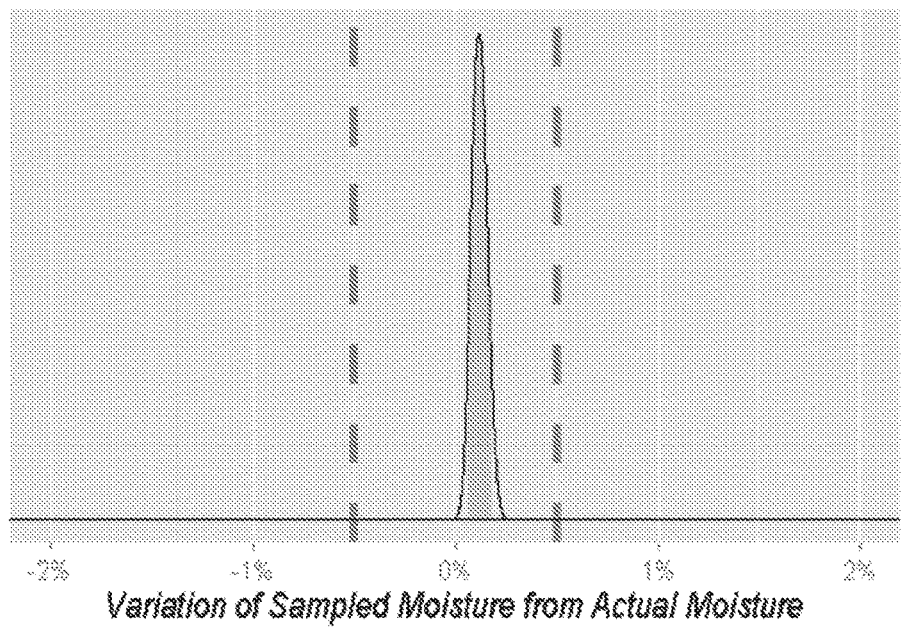
FIGS. 2A-2I are charts showing the statistical range and confidence intervals for well-mixed piles of aggregate having various moisture spreads.
Figure 2B:
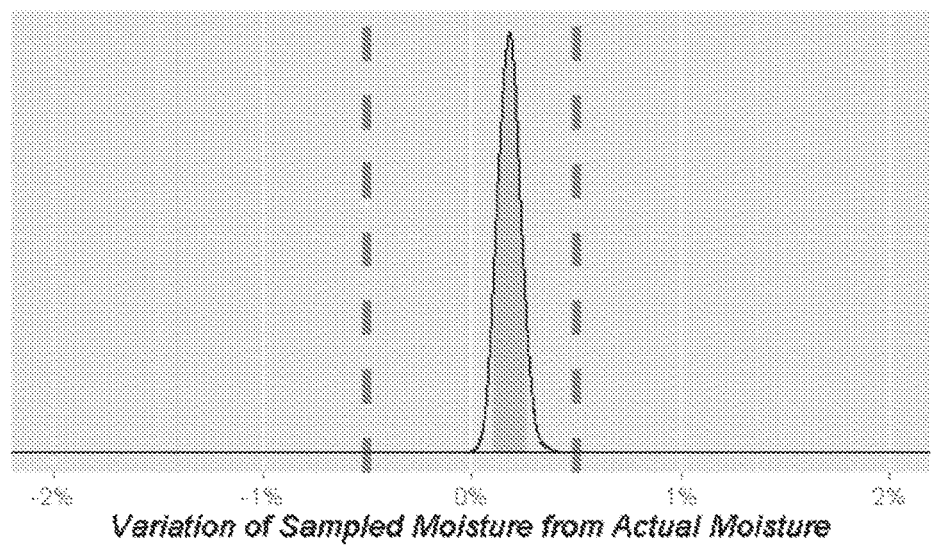
Figure 2C:
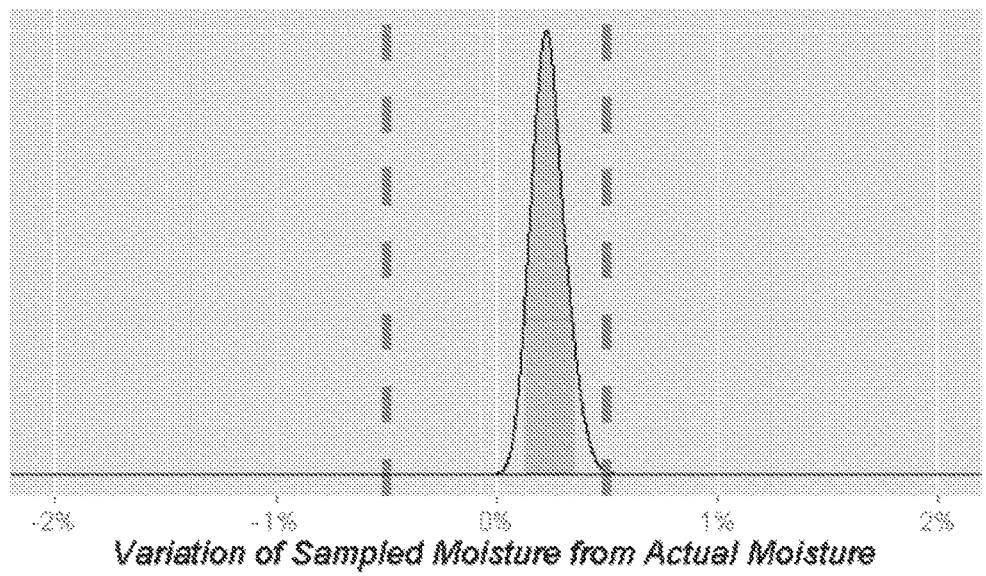
Figure 2D:
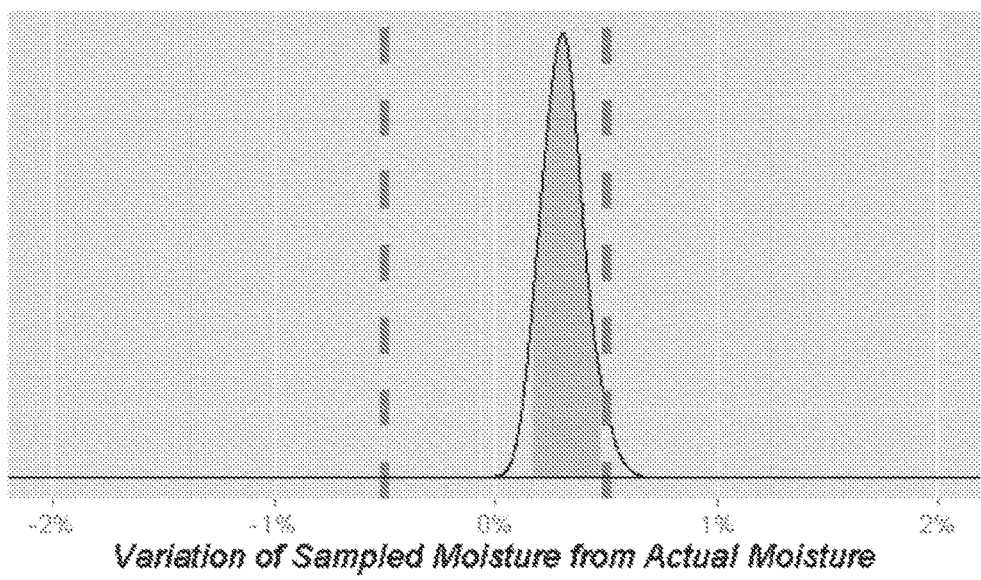
Figure 2E:
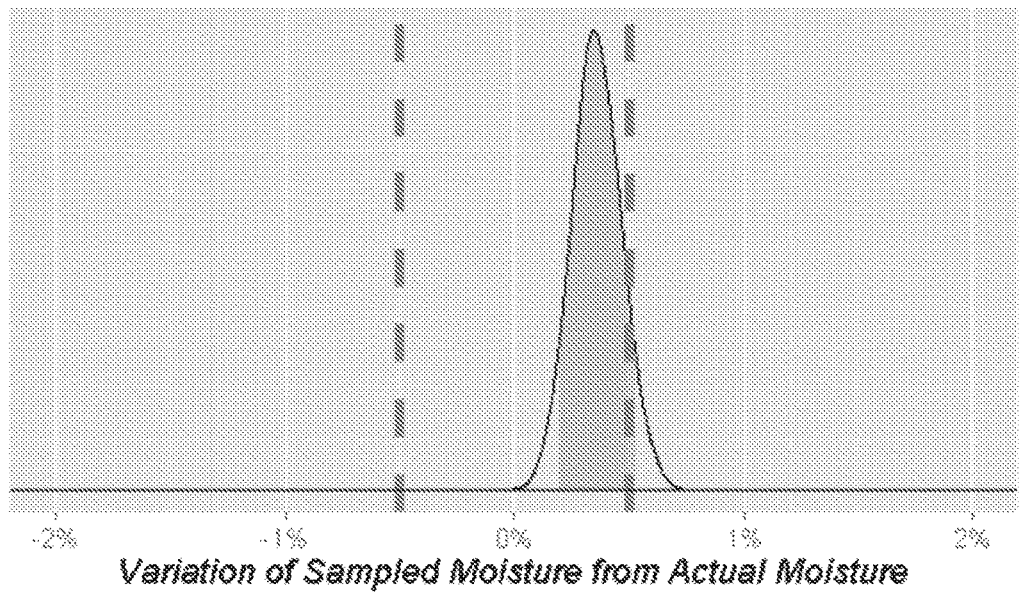
Figure 2F:
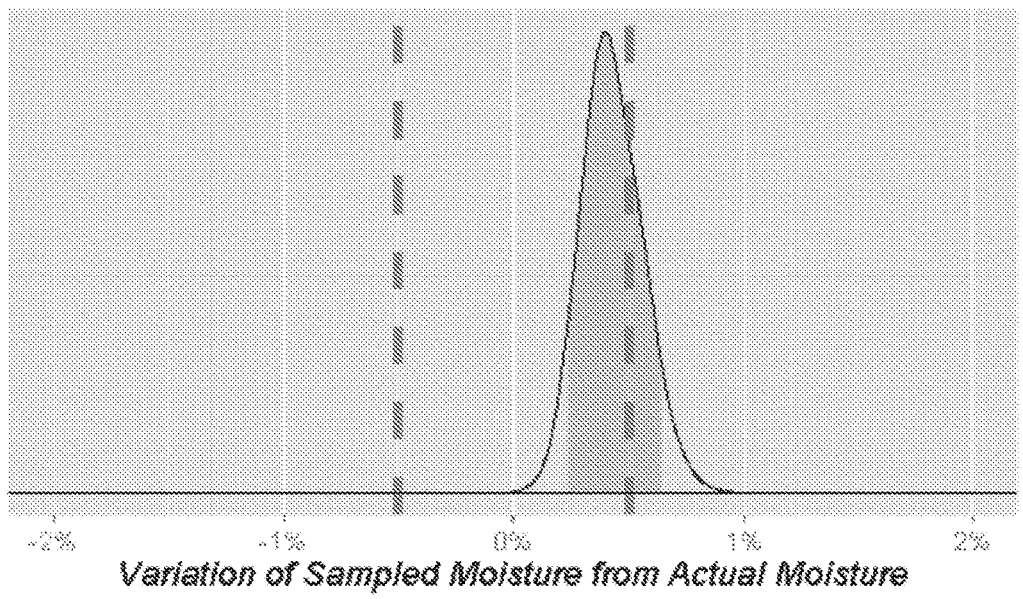
Figure 2G:
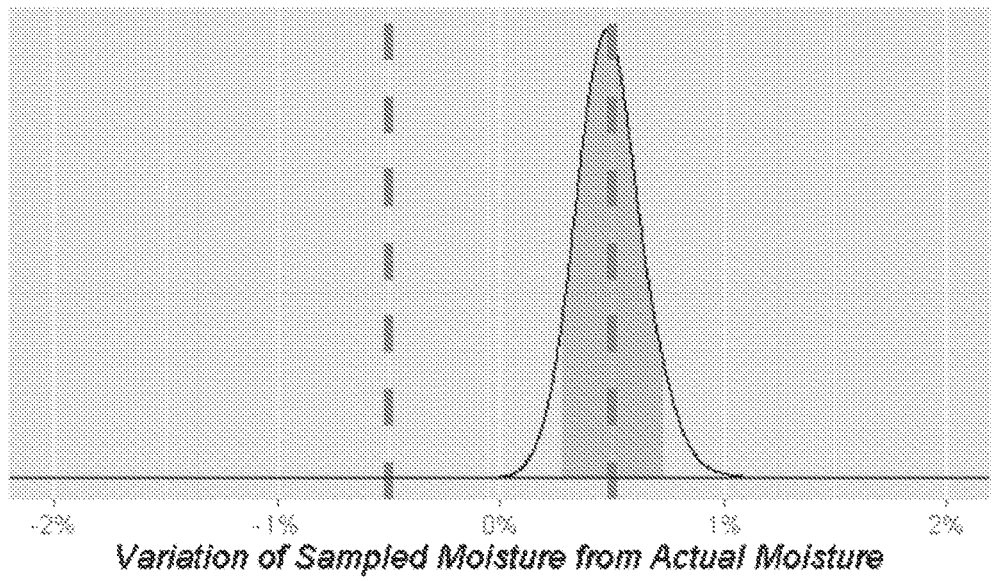
Figure 2H:
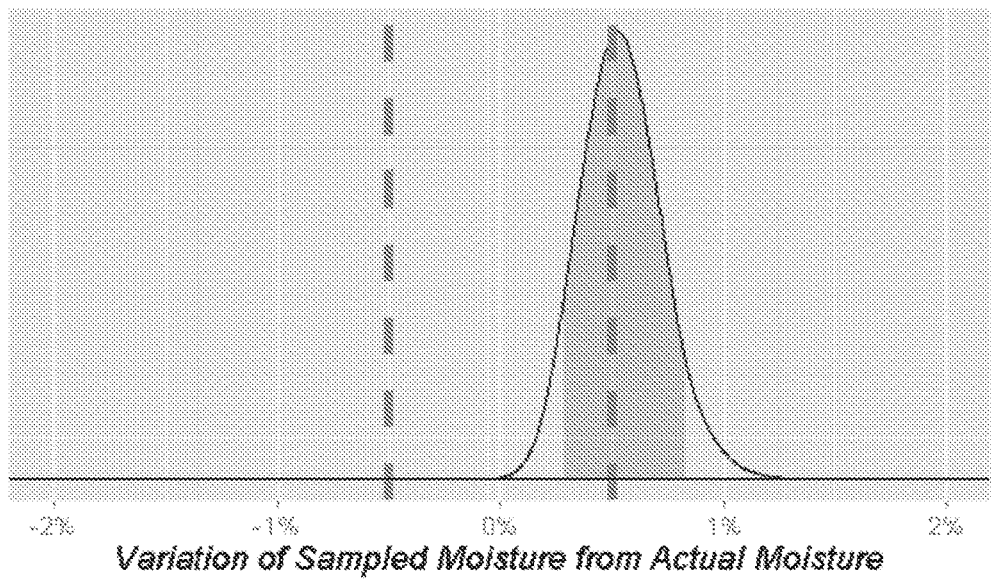
Figure 2I:
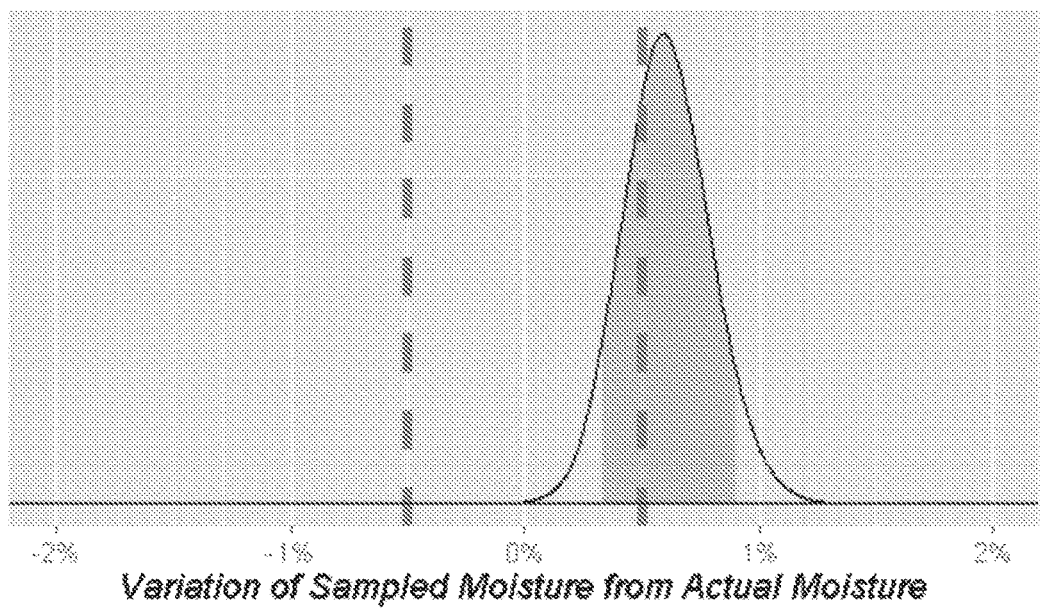
Figure 3A:
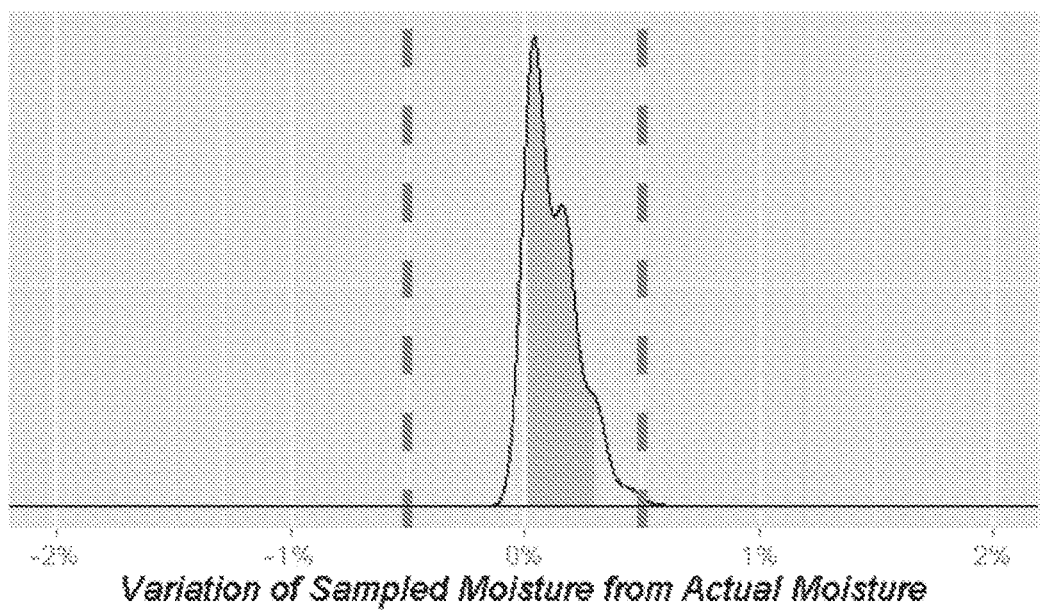
FIGS. 3A-3I are charts showing the statistical range and confidence intervals for poorly mixed piles of aggregate having various moisture spreads.
Figure 3B:
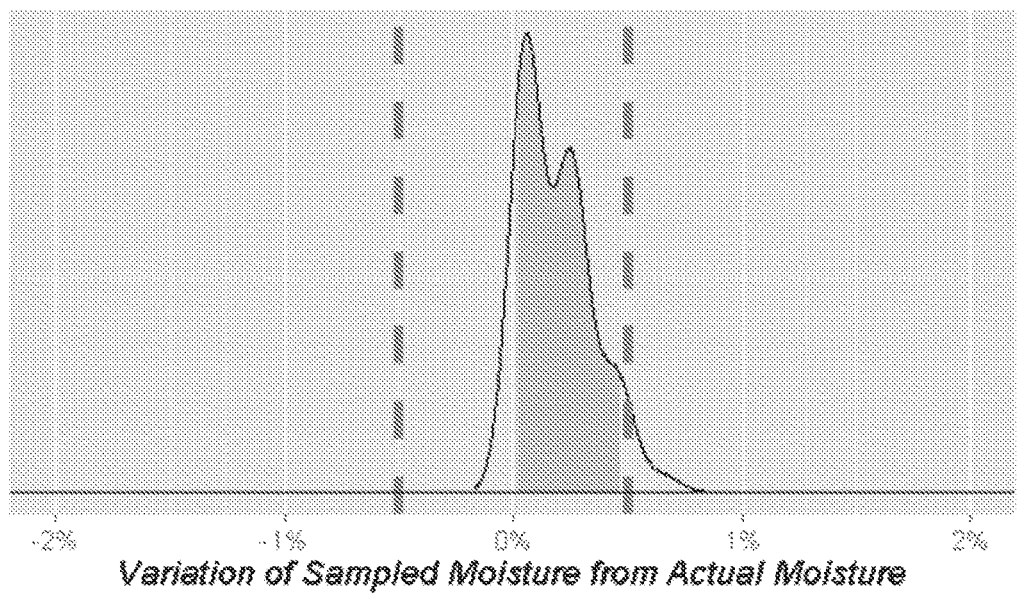
Figure 3C:
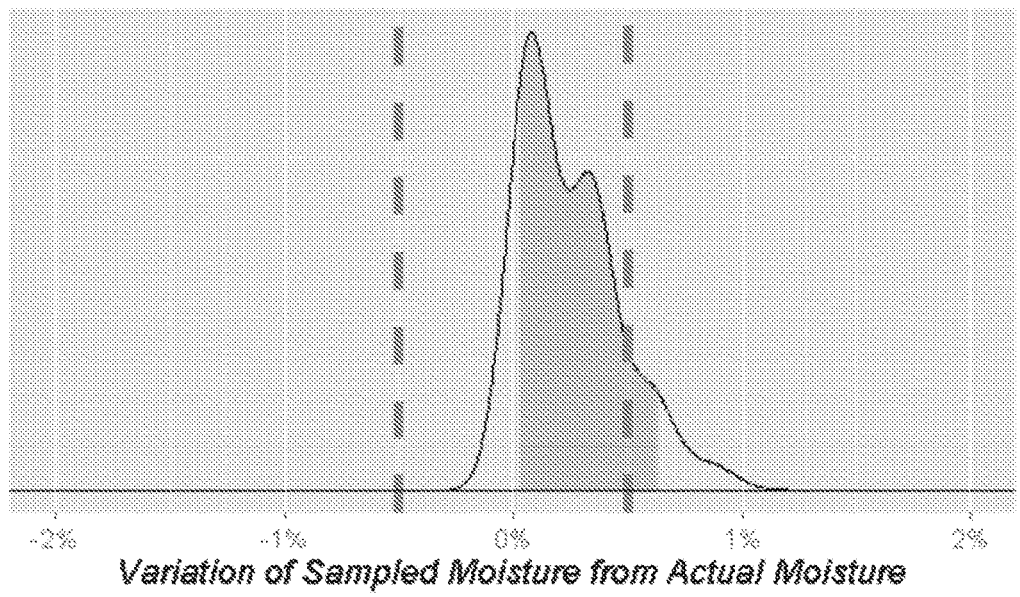
Figure 3D:
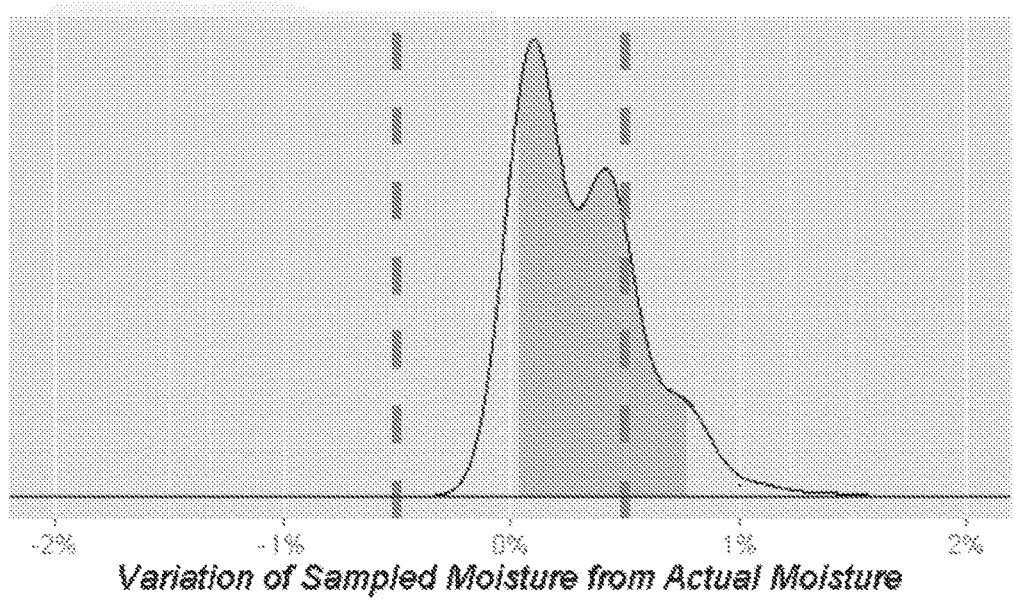
Figure 3E:
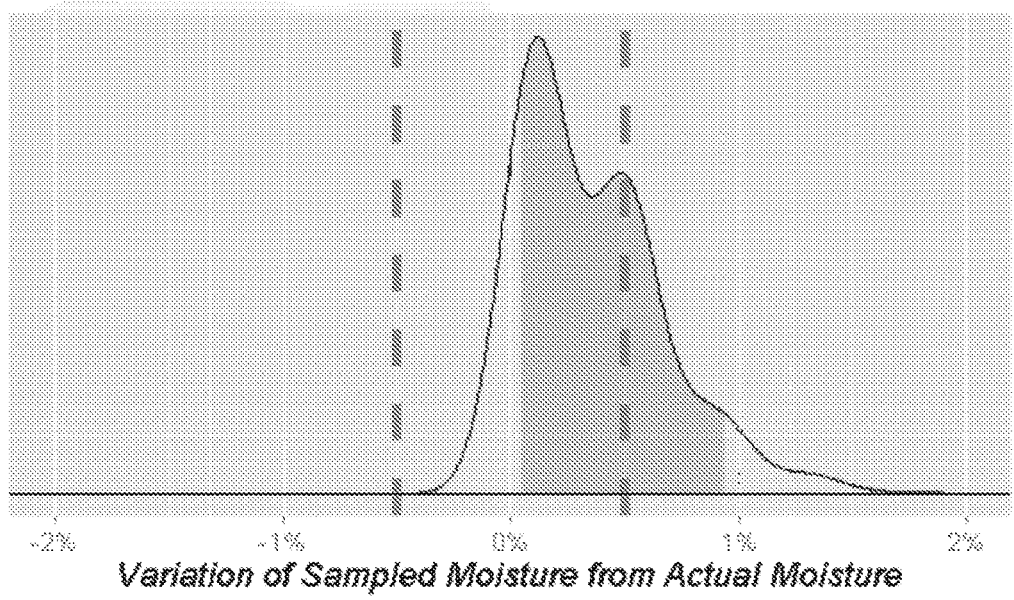
Figure 3F:
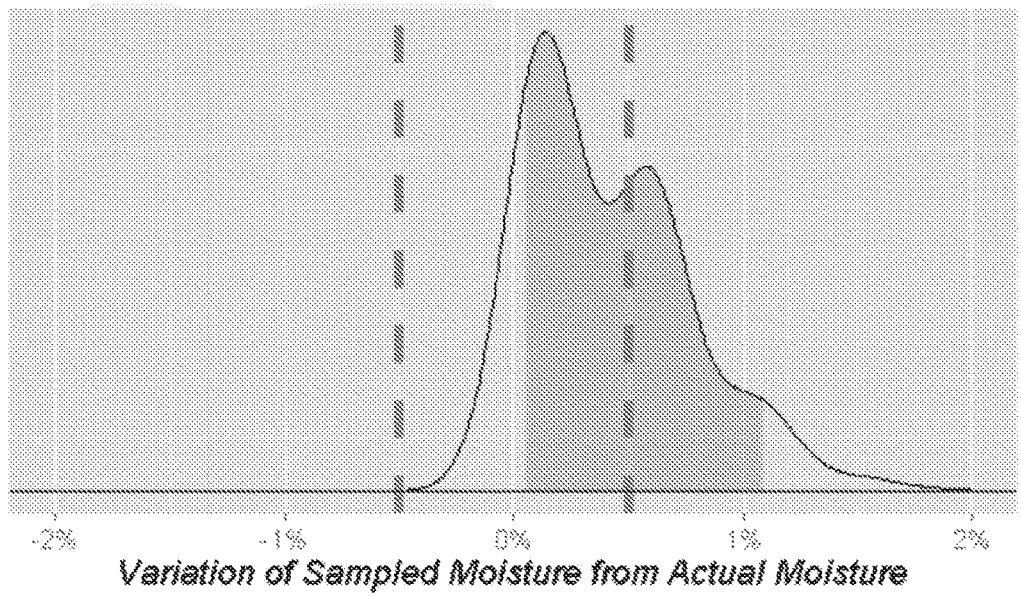
Figure 3G:
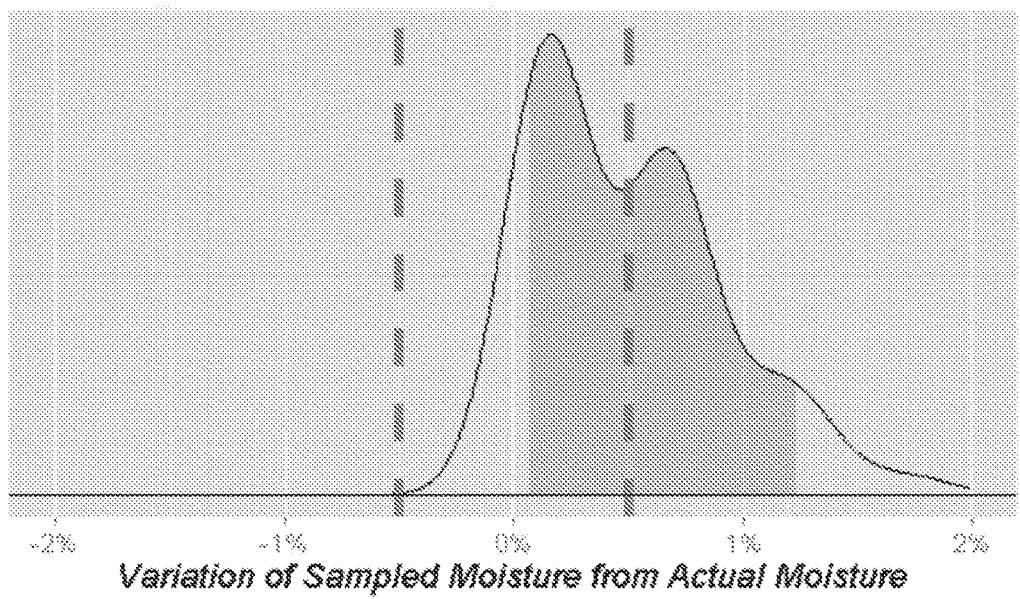
Figure 3H:
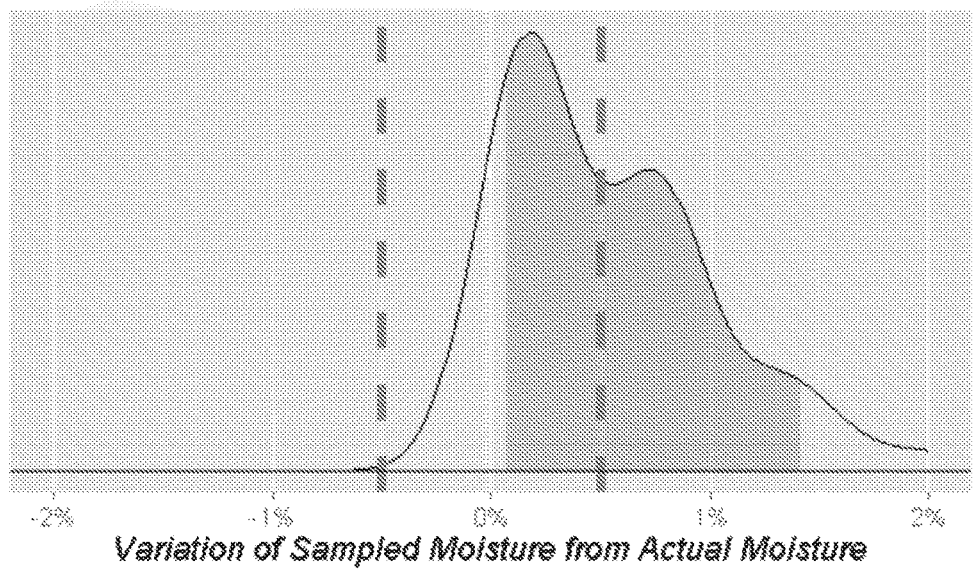
Figure 3I:
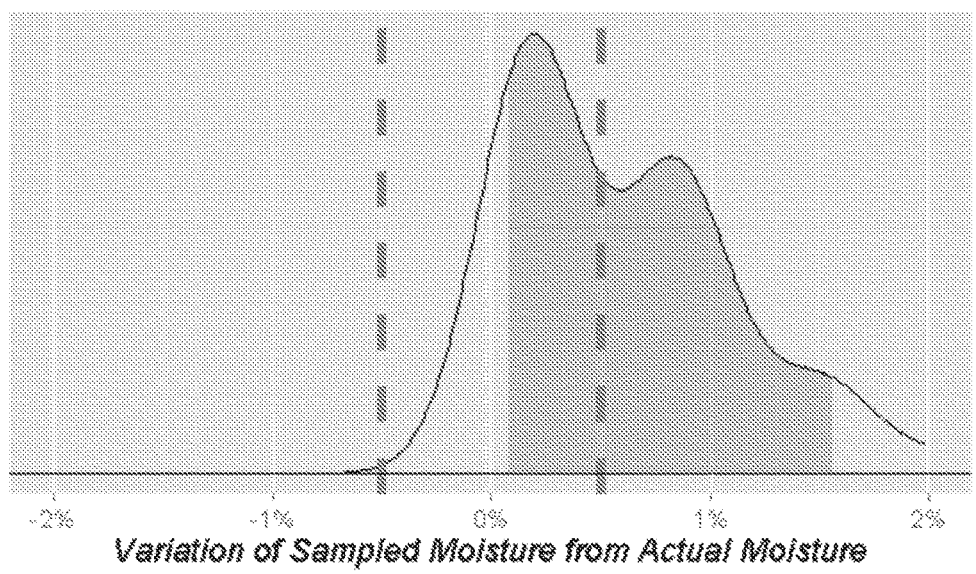

FIG. 1 depicts the general process for providing raw material into a dry batch concrete plant. The aggregate is typically stored in a pile 2 on location at the plant and left in the open air. When a batch of concrete is to be prepared aggregate is loaded from the storage pile 2 into a hopper 4, which is then conveyed up to one or more storage bins 6. The conveyor or hopper 4 dumps the aggregate into a storage bin 6. At the bottom of the storage bins 6 are moisture sensors 8, which determine the moisture content of the aggregate and which are discussed in detail further below. The aggregate is then released into the aggregate scale 10. The moisture sensor 8 may determine the moisture content either at the time the aggregate is sitting in the storage bin 6, or during the time the aggregate is released into the scale 10. The scale 10 measures the total weight of the aggregate material. In some embodiments, a decumulative scale (e.g., one in which the scale is filled and then weighed as amounts are removed). The aggregate is next conveyed to the collection funnel 12 and combined with water 16, cement 14, and chemical admixtures 18 to form the concrete mixture that is loaded into the back of a concrete truck 20.

For comparison, a typical wet mix plant also includes a mixer, which mixes all the materials together into a wet concrete batch before being dumped into a concrete truck. Otherwise, the plant is similar in operation to a dry batch plant.

Turning to the aggregate moisture, a typical moisture spread in a pile of aggregate material, from top to bottom, is about 5-6% (e.g., 2% moisture content at the top, and 7-8% moisture content at the bottom) which may be due to a number of factors (most of which the plant operator has little control over). The end result is a pile of material that is largely stratified in moisture content from top to bottom (i.e. a "poorly mixed" pile). The pile sometimes is mixed, i.e., the material is spread out on the ground, then mixed in a randomized fashion to blend the wetter and drier volumes of material, or subjected to other mechanical blending, then re-piled to form a "well-mixed" pile. When a well-mixed pile is left standing for a significant period of time, gravity again pulls moisture down and stratifies the pile into a poorly mixed pile again.

At the time of production, the piled material is loaded into a conveyor for delivery into the plant. When loading from a pile, the standard practice in the industry is to take portions of material from the top, middle, and bottom of the pile (whether well mixed or poorly mixed) in order to approximate an average amount of moisture. However, when the pile is poorly mixed, taking too much from the top or bottom can result in a blend of material that does not approximate the average moisture content of the pile. Alternatively, the material may be delivered and unloaded immediately and directly into the conveyor apparatus at the plant. This can result in a moisture distribution in the materials that is similar to a poorly mixed pile. The issues presented to the production process by a poorly mixed pile are discussed further below.

In a concrete plant, the proportioning of bulk materials is achieved by weighing the materials individually in one or more hopper scales. In most cases, the material is stored in overhead bins and the material falls via gravity directly into the hopper scale through a mechanical gate mechanism. Alternatively, the material may be delivered by a conveying mechanism directly into the scale, or the weight of the material can be determined by via an integral, static weigh belt, or decumulative weight mechanism. As the material moves through the process, a moisture measurement is taken to determine the moisture value of the material. Electronic moisture probes (also called moisture sensors) can either be mechanically mounted so as to be in constant contact with the material, or mounted in such a manner that the sensor has contact only when the material is flowing. In either case, the capture of the instantaneous moisture value may be performed continuously or at discrete time intervals. Depending upon the rules of the appropriate local regulatory body, the sensor may be used to deliver continuous moisture readings of the material as it transfers to the scale in the plant, or, it may be used to take a single "snapshot" of the material moisture at some point as the material feeds to the scale. In the latter case the snapshot value is defined to represent the average moisture of the entire batch of material. Moisture sensors typically have a measurement error at or near ±0.3 to ±0.5%.

If an electronic sensor is not available, the moisture must be manually sampled. The moisture content can then be determined by heating the sample until dry and measuring the moisture content by the loss in weight (e.g., a gravimetric analysis), or by use of commercial standalone products that use a chemical process within a sealed pressure vessel.

In a typical concrete production plant, once the aggregate is loaded into a hopper or bin, it is taken to be mixed with other ingredients to form the desired concrete batch. Therefore, the only practical opportunity to measure the moisture content of the material for each particular batch is during the movement of the material from the pile to a plant scale or weigh belt.

In order to determine the amount of water content delivered with the aggregate during production, the moisture sensor's readings will then be multiplied by the weight of the aggregate applicable to the moisture percentage reading. For example, if one moisture reading is taken for every 10 kgs of aggregate, and 50 kgs of aggregate are provided to for the concrete, then 5 moisture readings may be taken, as indicated by Table I.

TABLE I

| No. of 10 kg Sample | Moisture Reading |
|---|---|
| 1 | 2% |
| 2 | 5% |
| 3 | 4% |
| 4 | 7% |
| 5 | 7% |

In a scenario such as shown in Table I, the average moisture content (as a percentage of dry weight) of the 50 kgs of aggregate would be about 5%, or 2.4 kg of water in the aggregate, as determined by the formula [(wet weight−dry weight)/dry weight]. This amount of water would then be deducted from the water amount specified in the concrete mix formula to be added during the batch production process.

The frequency of moisture sensor readings and the correlated amount of aggregate relating to a particular sample can be varied as desired. Because moisture amounts can vary greatly even within a small sample (for example, when an amount of aggregate from the top of the pile is added, then an amount from the bottom of the pile immediately follows), more frequent readings generally provide a better determination of the actual amount of moisture. Moisture sensors typically output the moisture content in terms of the percentage water content of the aggregate as indicated in Table I.

Moisture sensors are calibrated using one of two methods. Some manufacturers use factory developed standards to calibrate the moisture sensor before it is delivered to the customer. With these factory calibrated sensors, the concrete producer is instructed to use the sensor to measure aggregate moisture without further adjustment. Other moisture sensors require field calibration, where the sensor is calibrated using a factory specified process to align the sensor response to the material(s) being measured for moisture. Field calibration may involve a recalibration of the sensor output signal (that is, the output signal is itself recalibrated to match the desired setting). Alternatively, the computational analysis of the sensor output signal may be modified so that a particular sensor output is calibrated to a new moisture measurement. In many systems, this involves modifying the regression analysis of the signal in order to calibrate that analysis to the manual sample reading. As used in this disclosure, a sensor calibration includes any of these mechanisms or procedures by which a sensor's output is related a given moisture amount; the calibration testing methods described herein are neutral as to any of these specific recalibration methods.

In any case, the moisture sensor operation needs to be periodically validated either for regulatory purposes, quality control assurance, concrete quality troubleshooting, or simply routine verification.

Moisture sensors are historically calibrated or verified at the production plant by comparing the reading of the sensor to a gravimetric analysis of a sample. For the calibration process, a moisture reading is captured from the sensor for a sample of aggregate. At the same time, a physical sample is manually captured. The physical sample is then subjected to a moisture test. One common gravimetric analysis used in the industry is referred to as a "bake out." In a bake out procedure, the sample is weighed to obtain an initial (wet) weight, then baked until the sample is completely dry. The dry sample is weighed again to obtain the dry weight. The difference between the sample's wet weight and dry weight is the weight of the water contained in the sample. This is usually divided by the dry weight reading (although in some jurisdictions the wet weight is used), and expressed in a percentage. For example, where a sample is found to have an initial (wet) weight of 500 grams and a dry weight of 475 grams, the water weight would be 25 grams and expressed as 5.26% (25 gm/475 gm×100%=5.26%) moisture (as a percentage of dry weight.) This process can take 30 minutes or more to properly dry a sample of material using the bake out method. Other gravimetric methods are provided by commercial, standalone products that use a chemical process within a sealed pressure vessel to measure the available water in the material and by calculation the percent of moisture. While the chemical method is faster, it has substantially higher error rates depending upon the reliability and training of the user. Whichever method is used, the user adjusts the moisture sensor's output signal to match the moisture amount determined manually for the sample.

The problem with the conventional mechanical sampling method is it is physically impractical to repeatedly gather a sample which accurately represents the moisture in a pile or of the material as it flows into a hopper scale or weigh belt. As described, there are many conditions that result in moisture variation in the pile, or where multiple trucks are unloading aggregate into the plant. Where a pile has an uneven moisture distribution, a limited number of manually acquired samples provides a very poor estimate of the material's true moisture percentage, and this problem increases as the moisture variation from top to bottom within the pile increases.

Historically, the calibration process instructed the user to run one or a handful of samples and from these limited samples, adjust the sensor reading to match. This usually occurred during the initial installation and could take a significant amount of time due to bake out process. Further, in most cases, after a period of time the user would typically begin to suffer from "sample fatigue" and would use a single test result and adjust the probe reading to match. This is a particularly poor practice for many reasons. First, with a poorly mixed pile taking a single sample and expecting that to represent the current moisture of the entire pile is likely to introduce inaccuracies. Second, as stated the bake out procedure can take 30 minutes to several hours depending on how rapidly the sample is processed. To use a sample bake out result from several hours prior and adjust the current moisture probe reading to match is highly unlikely to result in an accurate calibration.

Therefore, current practices do not provide for a repeatable, meaningful calibration or verification of moisture probes for two reasons. First, a small number of manual samples cannot be construed to represent the average moisture of material in a pile. Some statistically significant number of samples must be used in order to properly calibrate or verify the calibration of the probe. No current method for this process is in use today. Second, due to the amount of time it takes for accurate bake out results to be available, there must be a method to correlate the result of the physical sample with the electronic capture of the moisture by the sensor.

In order to understand the correlation between the moisture in a pile of material and the sampling of material taken from a production plant, a software simulator was built. The simulator assumed that 2,727 kg (6000 lbs.) of sand was being loaded, and that only about ½ kg (1 lb.) was randomly sampled from the stream. The difference in moisture content between the top and bottom of the pile was allowed to vary from a 10% spread (2% at the top vs. 12% at the bottom) to a 2% spread (2.5% at the top vs. 4.5% at the bottom). The moisture content for the middle was assigned between the values for the bottom and top, weighted to be closer to the top moisture content number to better reflect the field test results. Fifteen (15%) to 25% of the simulated load was allowed to come from the top, 72.25-80% was allowed to come from the middle, and 5.75-7.5% was allowed to come from the bottom of the pile, constrained so that the percentages summed to 100%—these percentages were allowed to vary at each trial in order to better approximate different loads being taken from a stockpile. The system then ran 1000 trials under both "well-mixed" and "poorly-mixed" conditions. The results are in Table II below. This table describes that on average, the expected error, between what the sensor reported as the moisture amount, and the result of bake out of the manual samples would be between 0.12% and 0.61% for a poorly mixed pile over the long term. While this amount seems and is negligible, this value represents the average value. The distribution of the sample values, and the inclusion of those in the probe calibration process, is what is relevant.

TABLE II

| Moisture Spread from top to bottom of pile | Average difference between sample and true moisture content of load | |
|---|---|---|
| | Well Mixed | Poorly-mixed |
| 10% | 0.61% | 0.61% |
| 9% | 0.56% | 0.53% |
| 8% | 0.49% | 0.49% |
| 7% | 0.42% | 0.40% |
| 6% | 0.36% | 0.37% |
| 5% | 0.30% | 0.30% |
| 4% | 0.24% | 0.24% |
| 3% | 0.18% | 0.18% |
| 2% | 0.12% | 0.12% |

FIGS. 2A-2I show the expected statistical range for a well-mixed pile over which the moisture content, as measured by gravimetric analysis. The x-axis shows the difference between the measured and the actual percentage moisture content (i.e., 0% means that the manual sample results would be exactly the same as the amount of moisture actually present (the "true amount"); 1% means the manual sample results would be 1% greater than the true amount. The dashed vertical lines represent an 0.5% error threshold (the typical amount of error that is deemed acceptable in the industry.) The smoothed line is the statistical probability curve that the manual moisture sample results will differ from the true amount by the particular percentage amount of moisture content of the line's location along the x-axis. The shaded region represents the portion under the statistical curve within which 95% of the manual moisture samples will fall. Table III summarizes the minimum and maximum error rates that bound the 95% shaded interval for well mixed piles having moisture spreads ranging from 2% to 10%. This analysis shows that under a well-mixed pile scenario, moisture bake out tests will differ from the true average moisture of the pile from a best case of 0.18% up to a worst case of 0.91%. Given that the sensor is more likely to be closer to the "true" amount because of continuous sampling, the manual sample and associated bake out can be outside of the desired 0.5% error threshold as compared to the sensor, yet the sensor still be properly calibrated.

TABLE III

| FIG. No. | Moisture Spread (Well-Mixed Pile) | 95% Range (Shaded Interval) for Moisture Sensor Error | |
|---|---|---|---|
| | | Lower Bound | Upper Bound |
| 2A | 2% | 0.06% | 0.18% |
| 2B | 5% | 0.1% | 0.27% |
| 2C | 4% | 0.14% | 0.37% |
| 2D | 7% | 0.17% | 0.48% |
| 2E | 7% | 0.2% | 0.53% |
| 2F | 7% | 0.24% | 0.64% |
| 2G | 8% | 0.28% | 0.73% |
| 2H | 9% | 0.28% | 0.83% |
| 2I | 10% | 0.34% | 0.91% |

The expected variance of moisture sample outcomes is even more acute when the sample is poorly mixed. The smoothed line in FIGS. 3A-3I is the statistical probability curve that the manual moisture sample results will differ from the true amount by the particular percentage amount of moisture content of the line's location along the x-axis. Three separate "bumps" in the bell curve can be seen in each of these charts. The shaded region represents the portion under the statistical curve within which 95% of the manual moisture samples will fall. Table IV summarizes the minimum and maximum error rates that bound the 95% shaded interval for poorly mixed piles having moisture spreads ranging from 2% to 10%. This analysis shows that under a poorly-mixed pile scenario, moisture bake out tests differ from the true average moisture of the pile from a best case of 0.31% up to a worst case of 1.57%. Again, given that the sensor is more likely to be closer to the "true" amount because of continuous sampling, the manual sample and associated bake out result can be outside of the desired 0.5% error threshold as compared to the sensor, yet the sensor still be properly calibrated.

TABLE IV

| FIG. No. | Moisture Spread (Poorly Mixed Pile) | 95% Range (Shaded Interval) for Moisture Sensor Error | |
|---|---|---|---|
| | | Lower Bound | Upper Bound |
| 2A | 2% | 0.02% | 0.31% |
| 2B | 5% | 0.02% | 0.47% |
| 2C | 4% | 0.03% | 0.63% |
| 2D | 7% | 0.04% | 0.78% |
| 2E | 7% | 0.05% | 0.94% |
| 2F | 7% | 0.05% | 1.09% |
| 2G | 8% | 0.07% | 1.24% |
| 2H | 9% | 0.07% | 1.42% |
| 2I | 10% | 0.08% | 1.57% |

As an example, suppose the pile is poorly mixed, and has an 8% variation in moisture. Because it is poorly mixed, the moisture content variations are stratified across the pile. The very top has a moisture content of 2%. Near the middle of the pile, the moisture content is about 6%. At the very bottom of the pile, the moisture content is 10%. Suppose that for a particular dump of aggregate onto the conveyor, equal amounts (each representing ⅓ of the total dump) are taken from the top, middle, and bottom. The resulting dump would have an average moisture content of 6%. Due to the continuous reading of the moisture probe of the material passing by, the moisture probe may in fact produce an average 6% reading. However, if a user was to attempt to capture a manual sample, and use the result of that single sample to affect a change to the calibration of the probe, that manual sample could be off by 1.2% either way from the true average moisture, as determined by the sensor. If the user only relied on that test, or a handful of tests, on material that originated from this pile the chances of arriving at the right average value for which to make an adjustment to or validate a sensor reading is very low.

The problem then is that the probe and the bake outs are not actually measuring material of the same moisture content; a small sample of the material taken manually for bake-out can have a very different moisture content than the entire load, especially when the moisture spread is large. As shown in FIGS. 3A through 3I and Table IV, the expected results of manual sample tests (with a 95% confidence interval, ignoring contributions due to sensor measurement error or error introduced by test personnel) can range from 0.31% to 1.57%.

Table V summarizes the maximum end of the error range for 95% of well-mixed and poorly mixed piles with moisture spreads from 2% to 10%, and further including a probe accuracy of 0.3%.

TABLE V

Includes Probe accuracy of ±0.3%

| Moisture Spread from top to bottom of pile | 95% of manual samples fall within this range plus or minus) from the true average | |
|---|---|---|
| | Well-mixed | Poorly-mixed |
| 10.00% | 1.21% | 1.87% |
| 9.00% | 1.13% | 1.72% |
| 8.00% | 1.03% | 1.54% |
| 7.00% | 0.94% | 1.39% |
| 6.00% | 0.83% | 1.24% |
| 5.00% | 0.78% | 1.08% |
| 4.00% | 0.67% | 0.93% |
| 3.00% | 0.57% | 0.77% |
| 2.00% | 0.48% | 0.61% |

The result of these findings is that even with a properly calibrated moisture sensor, there is a significant chance that the moisture content reading returned by the manual sample will likely exceed the 0.3-0.5% sensor measurement error threshold when in actual use. Therefore, a small or limited number of manual test results outside of the sensor measurement error do not indicate that re-calibration is needed, but rather an ongoing and continuous process of calibration/verification is needed.

Figure 4:
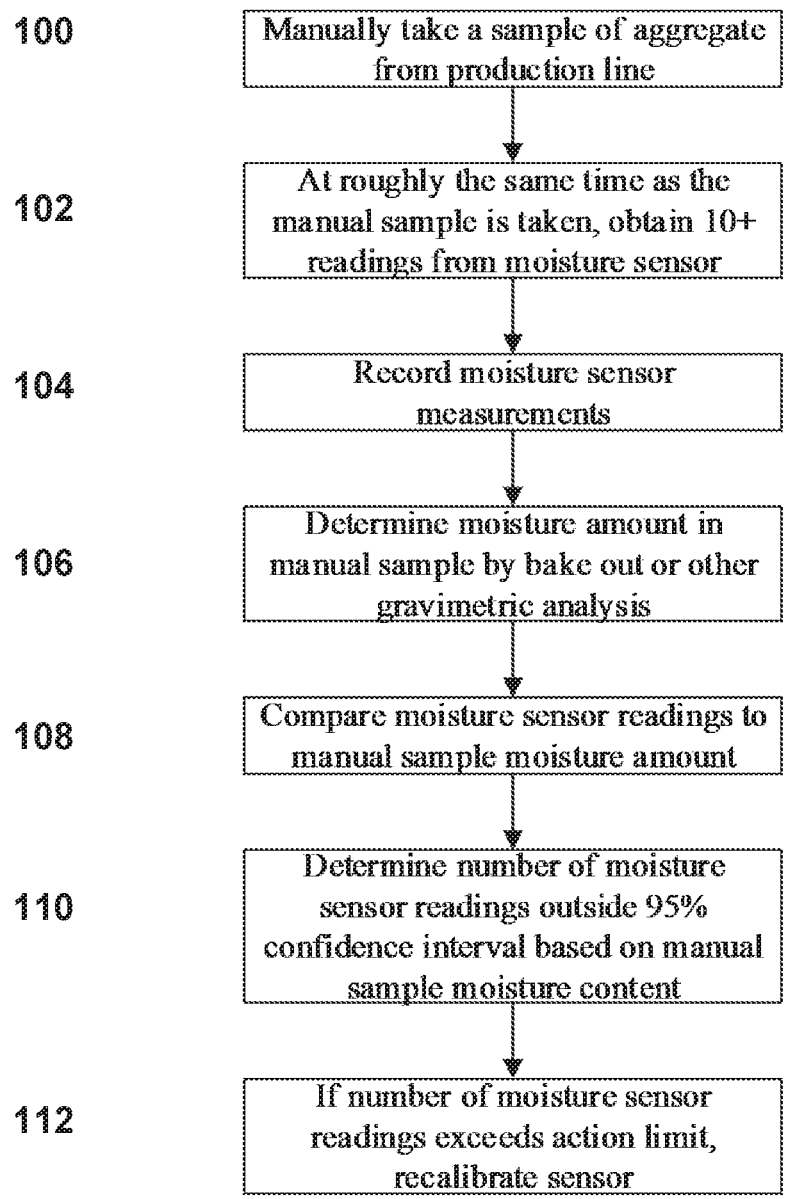
FIG. 4 depicts a process according to one embodiment of the disclosure.

In order to resolve this issue, a process for identifying such measurement issues during concrete production and responding to them has been developed. The general characteristics of this process are set forth in FIG. 4. In this process, multiple moisture sensor readings are taken in comparison to each single bake out or manual sample. The fact that multiple moisture sensor readings or measurements are taken allows for a better statistical analysis comparing the sensor to the bake-out, which takes advantage of the statistical ranges introduced by errors in the bake out process.

The process occurs during ongoing production of concrete. First, a statistically significant number of manual samples of aggregate are taken 100 from the production line. Each sample is taken at roughly the same time as a moisture sensor takes a reading 102, such that the sample is very similar in composition to the portion of the aggregate that is measured by the moisture sensor. These moisture sensor readings are recorded 104 in a database. The sample is taken at the same time as the moisture sensor reads the moisture content of the passing aggregate.

Each manual sample is then subjected to a gravimetric analysis (typically a bake-out as described above) to determine 106 the actual moisture content of the sample. This value is entered into a database for comparison with the moisture content reading taken by the moisture sensor.

Next the moisture content reading of the moisture sensor is compared 108 with the actual moisture content as determined by the gravimetric analysis to determine the moisture content differential. The differential is the difference between the actual and the sensor-measured moisture content. This differential is also recorded in the database. The differential is preferably stored as a percentage. For example, if, for a 500 gram sample, the actual moisture content is found to be 4.30%, and the sensed amount is found to be 5.25%, the differential is 0.95%. In this way, the moisture differential may be easily compared to the reading of the moisture sensor. Other information concerning the moisture differential (such as the actual difference in water content identified) may be stored as desired. The choice of which values to use and store as the moisture differential may be determined by such particular usage at any given plant.

As discussed above, for piles of aggregate having moisture variation, it is likely that manual moisture test results will vary between the 95% confidence interval. Therefore, any single or small number of moisture test results having a differential exceeding the error threshold of the sensor is not a cause for recalibrating the sensor or otherwise adjusting the process. A certain statistically significant number of tests should occur before any action is taken. This is the "action limit." The action limit is subject to user discretion, but preferably is based on the statistical sampling methods described above. For example, if the moisture limit is based on the 95% confidence interval, then the moisture sensors should read within the range of the bake out sample 95% of the time. Therefore, if 20 moisture sensor measurements are taken in reference to a single bake out sample, then 95% of the sensor measurements (that is, 19 of the 20) should be within the same range. Therefore the action limit in this scenario would be 2. If the number of readings outside the 95% confidence interval meets or exceeds 2 in this case, then the sensor should be recalibrated.

In brief, at least 10, and preferably between 15 and 20, test measurements are to be taken. The error between the sensor reading and the manual test results is recorded for each test. If the number of erroneous readings exceeds the action limit 110, then the sensor will need to be recalibrated 112.

If the sensor is in fact accurately reading the test samples (as verified by 95% of the most recent samples being within the ranges as specified in Table V then no calibration is needed, and the operator can rely on the sensor to adjust the water amount specified by the mix formula to be added to the concrete. This will ensure that the concrete conforms to the specified W/C ratio as well as maintaining the other desired characteristics.

Figure 5:
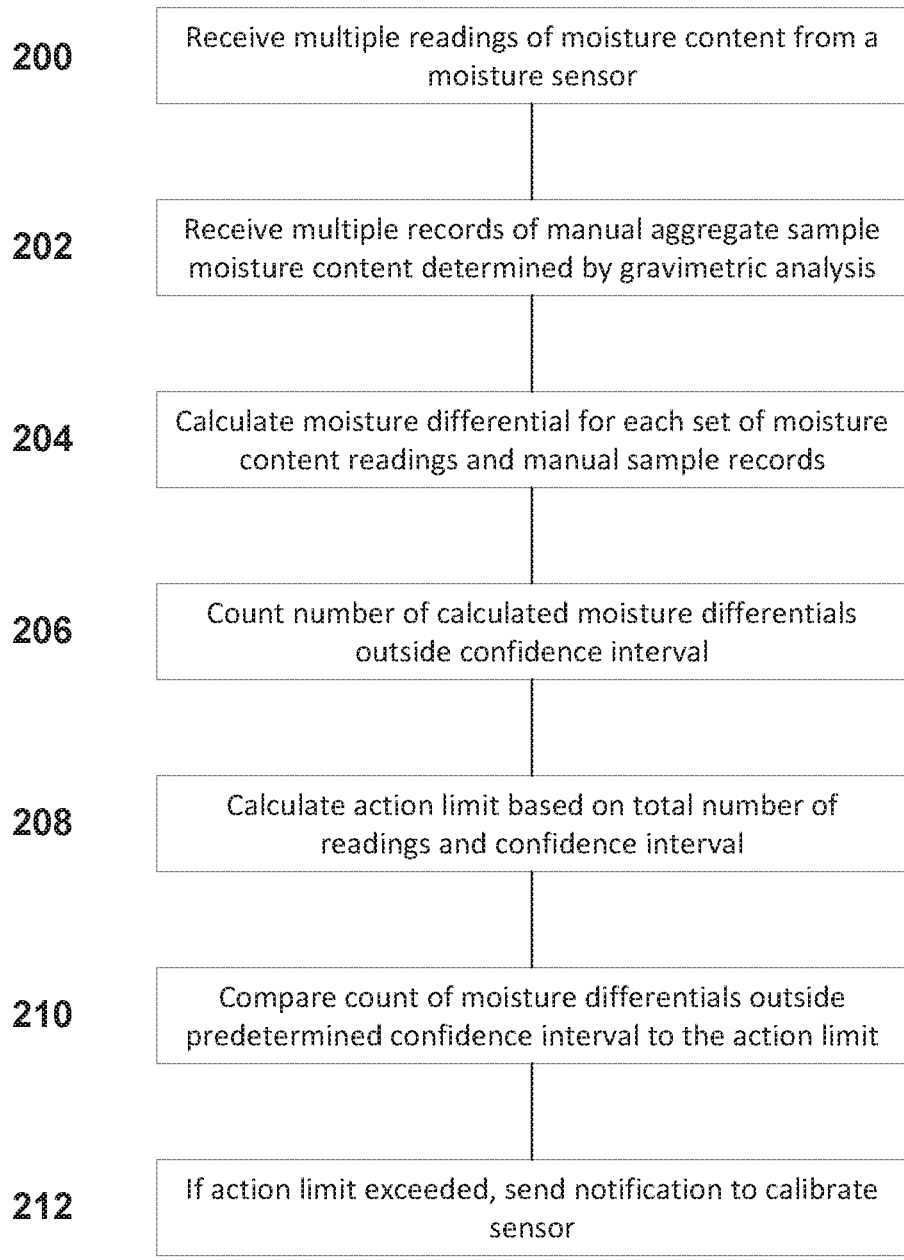
FIG. 5 depicts a process according to another embodiment of the disclosure.

FIG. 5 shows another process for calibrating the moisture sensors. Here, a computer containing memory and a database receives 200 readings of moisture content from the moisture sensor. Moisture content records from the gravimetric analysis samples are also received 202 into the database. A confidence level is also set by the user and entered into the database. Once a desired number of correlated sensor readings and sample records has been obtained, the computer processor calculates 204 the moisture differentials for each pair of readings and records. The number of moisture differentials outside the confidence interval are counted 206. After the action limit is calculated 208 based on the number of moisture sensor readings taken, the processor compares 210 the count of moisture differentials outside the confidence interval to the action limit. If the action limit is exceeded, a notification is sent or displayed 212 to calibrate the sensor.

A computerized system for determining the calibration of a moisture sensor can speed the described process. In this discussion, the term "storage device" as used herein refers to a machine-readable device that retains data that can be read by mechanical, optical, or electronic means, for example by a computer. Such devices are sometimes referred to as "memory," although as used herein a machine-readable data storage device cannot comprise a human mind in whole or in part, including human memory. A storage device may be classified as primary, secondary, tertiary, or off-line storage. Examples of a storage device that is primary storage include the register of a central processing unit, the cache of a central processing unit, and random-access memory (RAM) that is accessible to a central processing unit via a memory bus (generally comprising an address bus and a data bus). Primary storage is generally volatile memory, which has the advantage of being rapidly accessible. A storage device that is secondary storage is not directly accessible to the central processing unit, but is accessible to the central processing unit via an input/output channel. Examples of a storage device that is secondary storage include a mass storage device, such as a magnetic hard disk, an optical disk, a drum drive, flash memory, a floppy disk, a magnetic tape, an optical tape, a paper tape, and a plurality of punch cards. A storage device that is tertiary storage is not connected to the central processing unit until it is needed, generally accessed robotically. Examples of a storage device that is tertiary storage may be any storage device that is suitable for secondary storage, but configured such that it is not constantly connected to the central processing unit. A storage device that is off-line storage is not connected to the central processing unit, and does not become so connected without human intervention. Examples of a storage device that is off-line storage may be any storage device that is suitable for secondary storage, but configured such that it is not constantly connected to the central processing unit, and does not become so connected without human intervention. Secondary, tertiary, and offline storage are generally non-volatile, which has the advantage of requiring no source of electrical current to maintain the recorded information.

A storage device cannot be construed to be a mere signal, although information may be communicated to and from a storage device via a signal.

The term "telecommunications network" as used herein refers to a network capable of transferring information spatially by conducting signals, such as but not limited to electrical or optical signals. The network itself cannot be construed to be a mere signal. The "optical" signal need not comprise radiation in an optically visible wavelength, and may be in any suitable wavelength. The network may be a packet-switched network (such as a local area network or the Internet) or a circuit-switched network (such as some telephone networks or the global system for mobile communications (GSM)). Information sent via a packet-switched network may be for example electronic mail, an SMS text message, and a digital file sent via file transfer protocol (FTP). Information sent via a circuit-switched network may be for example a voice mail message, a facsimile message, an SMS text message, or a digital file.

The term "processor" or "central processing unit" (CPU) as used herein refers to a software execution device capable of executing a sequence of instructions ("program"). The CPU comprises an arithmetic logic unit, and may further comprise one or both of a register and cache memory.

The term "variable" as used herein refers to a symbolic name corresponding to a value stored at a given memory address on a data storage device (although this address may change). The value may represent information of many types, such as integers, real numbers, Boolean values, characters, and strings, as is understood in the art. As used herein the value of a variable is always stored in a data storage device, and shall not be construed to refer to information only stored in a human mind. Any recitation of a variable implicitly requires the use of a data storage device.

The term "machine-readable format" as used herein refers to a medium of storing information that is configured to be read by a machine. Such formats include magnetic media, optical media, and paper media (punch cards, paper tape, etc.). Printed writing in a human language, if not intended or configured to be read by a machine, is not considered a machine readable format. In no case shall a human mind be construed as "machine readable format."

The term "database" as used herein refers to an organized data structure comprising a plurality of records stored in machine-readable format.

A system for performing the processes described above links each moisture sensor through a telecommunications network to a storage device containing a database for recording the moisture sensor readings. Moisture sensors today can be converted to a digital output, and so this only requires directing the output of each sensor to the appropriate database. Separately, the results of testing manual samples through the bake out or other moisture-measuring procedure are also added to the database for comparison with the moisture sensor readings. Recorded in the database are multiple (at least 10, and preferably 15-20) moisture sensor readings per baked out manual sample result pair for the material. In order to determine the calibration state of a sensor, the processor retrieves from the database in the storage device the manual sample test results and the correlated multiple moisture sensor readings obtained from the aggregate in the plant. These are compared to determine the differential of each moisture sensor reading, and that differential is compared to the allowed ranges set forth in Table V. Where a statistically significant number of samples exceed the 95% ranges in Table V, then the processor can set a flag for the operator indicating that the particular moisture sensor needs to be recalibrated. Therefore, by continuing to take periodic samples, i.e., as part of routine maintenance, on an ongoing basis the correct calibration of the probe can be continuously confirmed.

While the invention has been described with respect to a limited number of embodiments, those skilled in the art, having benefit of this disclosure, will appreciate that other embodiments can be devised which do not depart from the scope of the invention as disclosed here.

I claim:

1. A process for monitoring and re-calibrating a moisture sensor during production runs of concrete, comprising:
 a) obtaining a manual sample of aggregate;
 b) at roughly the same time as obtaining the manual sample, taking multiple readings of moisture content using a moisture sensor;
 c) recording the multiple moisture sensor readings;
 d) determining the moisture content of the manual sample;
 e) recording the moisture content of the manual sample;
 f) comparing the recorded manual sample moisture content to each of the recorded moisture content readings to obtain a moisture differential for each sensor reading;
 g) where the moisture differential exceeds a 95% confidence interval, counting the sample against an action limit;
 h) where the number of samples having a moisture differential exceeding the 95% confidence interval meets or exceeds the action limit, recalibrating the sensor.

2. An automated process for monitoring and re-calibrating a moisture sensor during production runs of concrete, comprising:
 a) receiving multiple readings of moisture content in a load of aggregate from a moisture sensor, the load being one from which a manual sample has been taken for gravimetric analysis;
 b) receiving a moisture content record comprising the moisture content identified in the manual sample;

c) calculating a moisture differential for each reading by comparing the reading to the moisture content record;
d) counting the number of moisture differentials that are outside a predetermined confidence interval;
e) calculating an action limit from the total number of readings taken and the confidence interval;
f) comparing the count of moisture differentials outside the predetermined confidence interval to the action limit; and
g) when the count exceeds the action limit, indicating that the moisture sensor needs re-calibration.

3. The process of claim 2, where the predetermined confidence interval is at least 95%.

4. The process of claim 3, where the number of readings of moisture content is at least 20.

5. The process of claim 2, where the predetermined confidence interval is at least 90%.

6. The process of claim 5, where the number of readings of moisture content is at least 10.

7. A system for calibrating a moisture sensor used in concrete production, the system comprising:
a) a moisture sensor;
b) a transmitter in communication with the moisture sensor to transmit information to a database;
c) the database configured to record readings of moisture content from the moisture sensor, a moisture content record from a gravimetric analysis, and a confidence interval;
d) a display; and
e) a processor configured to
  i) calculate a moisture differential for each reading in the database by comparing the reading to the moisture content record;
  ii) count the number of calculated moisture differentials that are outside the predetermined confidence interval;
  iii) calculate an action limit from the total number of readings taken and the confidence interval;
  iv) compare the count of moisture differentials outside the predetermined confidence interval to the action limit; and
  v) if the count of moisture differentials outside the predetermined confidence interval exceeds the action limit, display on the display an indicator that the moisture sensor needs recalibration.

* * * * *